United States Patent

Ayer et al.

[11] Patent Number: 5,858,407
[45] Date of Patent: *Jan. 12, 1999

[54] METHOD FOR ADMINISTERING TANDOSPIRONE

[75] Inventors: Atul Devdatt Ayer, Palo Alto, Calif.; Dana A. Ridzon, San Francisco, Calif.

[73] Assignee: Alza Corporation, Palo Alto, Calif.

[*] Notice: The portion of the term of this patent subsequent to Feb. 9, 2010, has been disclaimed.

[21] Appl. No.: 179,393

[22] Filed: Jan. 10, 1994

Related U.S. Application Data

[63] Continuation-in-part of Ser. No. 10,086, Jan. 27, 1993, Pat. No. 5,330,762, which is a continuation-in-part of Ser. No. 842,682, Jan. 27, 1992, Pat. No. 5,185,158.

[51] Int. Cl.$^6$ ............................................. A61K 9/24
[52] U.S. Cl. ............................................. 424/473
[58] Field of Search ............................................. 424/473

[56] References Cited

U.S. PATENT DOCUMENTS

| | | | |
|---|---|---|---|
| 2,799,241 | 7/1957 | Wurster | 118/24 |
| 2,909,462 | 10/1959 | Warfield et al. | 167/56 |
| 3,845,770 | 11/1974 | Theeuwes et al. | 128/260 |
| 3,916,899 | 11/1975 | Theeuwes et al. | 128/260 |
| 4,016,880 | 4/1977 | Theeuwes et al. | 128/260 |
| 4,063,064 | 12/1977 | Saunders et al. | 219/121 L |
| 4,088,864 | 5/1978 | Theeuwes et al. | 219/121 LM |
| 4,200,098 | 4/1980 | Ayer et al. | 128/260 |
| 4,285,987 | 8/1981 | Ayer et al. | 427/3 |
| 4,327,725 | 5/1982 | Cortese et al. | 128/260 |
| 4,507,303 | 3/1985 | Ishizumi et al. | 514/255 |
| 4,708,868 | 11/1987 | Brickl et al. | 924/80 |
| 4,783,337 | 11/1988 | Wong et al. | 424/468 |
| 4,851,232 | 7/1989 | Urquhart et al. | 424/469 |
| 4,892,778 | 1/1990 | Theeuwes et al. | 428/218 |
| 5,011,841 | 4/1991 | Scappaticci | 514/253 |
| 5,057,321 | 10/1991 | Edgren et al. | 424/413 |
| 5,082,668 | 1/1992 | Wong et al. | 424/473 |
| 5,096,716 | 3/1992 | Deters et al. | 424/473 |
| 5,124,346 | 6/1992 | Seymour | 514/397 |
| 5,189,037 | 2/1993 | Seymour | 514/252 |

*Primary Examiner*—D. Gabrielle Brouillette
*Attorney, Agent, or Firm*—Paul L. Sabatine; Michael J. Rafa; Susan K. Thomas

[57] ABSTRACT

A dosage form is provided for administering a drug of the formula

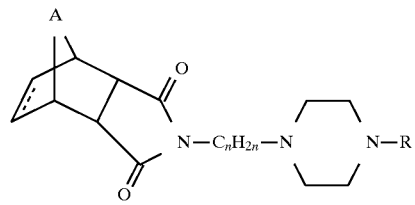

to a patient to produce an anxiolytic benefit in the patient. A method is provided for administering the drug of the formula for producing the intended therapy.

5 Claims, 5 Drawing Sheets

METHOD FOR ADMINISTERING TANDOSPIRONE

CROSS-REFERENCE TO RELATED APPLICATIONS

This application is a continuation-in-part of U.S. Ser. No. 08/010,086 filed Jan. 27, 1993 now U.S. Pat. No. 5,330,762 which U.S. Ser. No. 08/010,086 is a continuation-in-part of U.S. Ser. No. 07/842,682 filed Feb. 27, 1992 and now U.S. Pat. No. 5,185,158 issued Feb. 9, 1993. This application is with U.S. Ser. No. 07/942,899 filed Sep. 10, 1992 now U.S. Pat. No. 5,246,710 issued Sep. 21, 1993 and with U.S. Ser. No. 07/943,618 filed Sep. 10, 1992 now U.S. Pat. No. 5,246,711 issued Sep. 21, 1993, and with PCT/US93/09627 filed Nov. 8, 1993, and benefit is claimed of their filing dates.

FIELD OF THE INVENTION

This invention pertains to a novel and useful dosage form comprising the therapeutic drug represented by the general formula:

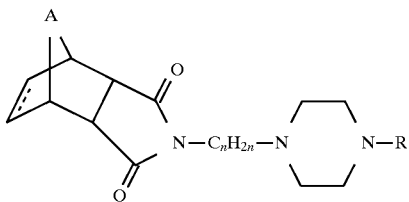

The invention concerns also a method for treating depressive disorders by administering the dosage form for delivering the drug of the general formula to a patient in need of antidepressive therapy. The invention relates also to novel compositions comprising the general formula, which compositions are useful for manufacturing the dosage form.

BACKGROUND OF THE INVENTION

A health need exits for a dosage form comprising the therapeutically active drug of the general formula (1): in either exo or endo form, the base, and pharmaceutically acceptable salts thereof:

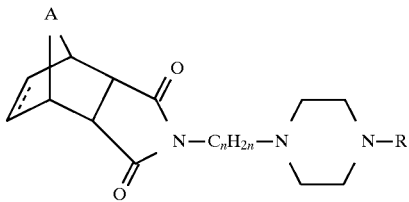

especially for a dosage form that exhibits an essentially zero order release rate of the drug over a long period of time. In formula (1), A is a member selected from the group consisting of an oxygen atom, a methylene group and an ethylene group, the full line embracing a broken line (— — —) designates either a single bond or a double bond, R is a phenyl group optionally substituted with a member selected from the group consisting of halogen, an alkyl group of 1 to 4 carbons, an alkoxy group of 1 to 4 carbons, a trifluoromethyl group, a 2-pyridyl group and a 2-pyrimidinyl group, and wherein n is an integer of 3 or 4.

A presently preferred drug embraced by formula (1) is represented by formula (2).

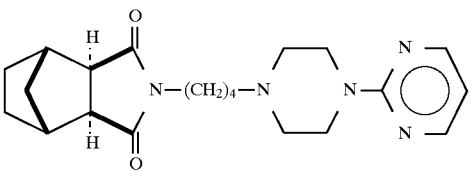

The drug depicted by formula (2) is known also as tandospirone, or by the name 4,7-methano-1H-isoindole-1,3(2H)-dione, hexahydro-2[4-[-(2-pyrimidinyl)-1-piperazinyl]butyl]-$(3a\alpha,4\beta,7\beta,7a\alpha)$-2-hydroxy-1,2,3-propanetricarboxylate (1:1) or as N-[4-[4-(2-pyrimidinyl)-1-piperazinyl]butyl-2,3-norbornanedicarboximide; and the base and pharmaceutically acceptable salts thereof. The drugs of both formulae are taught in prior art patents U.S. Pat. Nos. 4,507,303; 4,543,355; 4,598,078 and 5,011,841. The beneficial drugs of the formulae are administered by the prior art in rapid release manufactures, such as tablet, capsule, syrup and suspension. With such rapid release manufactures, the drug is administered by repeated administration to produce a therapeutic level.

Generally, for rapid release manufactures, as known to the prior art also as instant release dosage forms, the release rate profile follows the cube root law, that is, the release rate decreases with time, *Inter. J. Pharm.*, Vol. 62, pp 143–151, 1990. This release rate pattern provides unpredictable therapy and it is often accompanied by a period of time, when the patient is not receiving the drug. A critical health need exists for a controlled-release dosage form that overcomes the shortcomings known to the prior art. A controlled-release dosage form provides drug continuously to the patient for constant therapy for better health. A dosage form made with controlled-release drug delivery properties, provides drug at a controlled rate as a zero order plot of the rate of release of drug versus time shows an essentially straight line that indicates the rate of release is independent of time. A dosage form, according to the present invention, that provides for the controlled-rate of administration of drugs of formulae of (1) and (2), would represent a major advancement to the drug delivery art, because the controlled and extended zero order release of drug in a known and uniform dose over a long period of time reinforces better therapy.

In light of the above presentation, it will be evident to those versed in the dispensing art, that a pressing need exists for a dosage form possessing a zero order controlled rate of release that can deliver the valuable drug of formulae 1 and 2 for its therapy. The pressing need exists for a dosage form having a zero order controlled-rate of release, which controlled-rate is generated by osmotic diffusion, bioerosion, or ion-exchange activity, while simultaneously maintaining the physical and chemical integrity of the dosage form during the drug delivery period.

OBJECTS AND ASPECTS OF THE INVENTION

Accordingly, in view of the above presentation, it is an immediate object of this invention to provide a dosage form for delivering, at an essentially controlled rate of release, the drug of formulae (1) and (2) to a patient in need of formulae (1) and (2) drug therapy.

Another object of the present invention is to provide a controlled-order dosage form that substantially overcomes the deficiencies associated with the prior art.

Another object of the present invention is to provide a dosage form for administering formulae (1) and (2) drug at a controlled rate of release dose over a prolonged period of time for treating depressive disorders.

Another object of the present invention is to provide a dosage form that makes available zero order extended and controlled tandospirone therapeutic activity for anxiolytic therapy.

Another object of the invention is to provide a novel dosage form manufactured as an osmotic diffusion, bioerodable or ion-exchange dosage form that can administer a drug embraced by formula (1) at a rate controlled by the dosage form to a biological receptor site to produce the desired pharmaceutical effects.

Another object of the invention is to provide a novel dosage form manufactured as an osmotic diffusion, bioerosion or ion-exchange dosage form that can administer tandospirone at a controlled rate to a biological receptor site to produce the desired pharmaceutical effects.

Another object of the present invention is to provide a dosage form that substantially reduces and/or substantially eliminates the unwanted influences of the gastrointestinal environment of use and still provides controlled administration of formulae (1) and (2) drugs over time.

Another object of the present invention is to provide a dosage form that maintains its physical and chemical integrity during the delivery of tandospirone over an extended time up to 24 hours.

Another object of the present invention is to provide a dosage form adapted for oral administration of tandospirone, which dosage form comprises a first tandospirone composition and a second push composition that act together for the rate controlled administration of tandospirone to a patient over time.

Another object of the present invention is to provide a composition of matter comprising tandospirone, which composition is useful for manufacturing a dosage form.

Another object of the present invention is to provide a complete pharmaceutical regimen comprising a composition comprising tandospirone that can be dispensed from an osmotic diffusion, bioerodable or ion-exchange delivery device, the use of which requires intervention only initiation and possibly for the termination of the regimen.

Another object of the invention is to provide a method for treating depressant disorder comprising administering an antidepressant effective dose of tandospirone from a zero order dosage form, to a warm-blooded animal.

Another object of the invention is to provide the use of a dosage form for administering tandospirone from a dosage form at an osmotically-powered rate, a diffusional-powered rate, a bioerodable-powered rate, or an ion-exchange powered rate over time, wherein the tandospirone is selected from the group consisting of a base, a salt, an endo and an exo form.

Another object of this invention is to provide a novel method of manufacturing poly(ethylene oxide)-containing formulations for use in drug delivery devices.

Another object of the invention is to provide a method of administering anti-anxiety tandospirone from a dosage form that releases tandospirone over 24 hours.

In one aspect of the present invention there is provided a therapeutic composition comprising a proportion of a drug of the following formula:

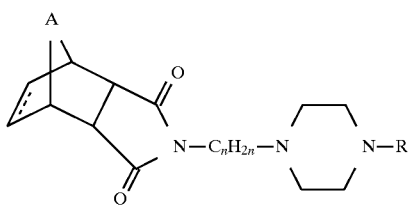

in which A is oxygen, a methylene group or an ethylene group, the full line embracing a broken line is either a single or a double bond, R is a member selected form phenyl, phenyl substituted with a halogen a, $C_1$ to $C_4$ alkoxy, a trifluoromethyl, a 2-pyridyl, and a 2-pyrimidinyl group; and n is 3 to 4; and a polymer composition comprising the repeating molecular unit $—(—CH_2CH_2—)_n—$ where n is 4500 to 7500.

In another aspect of the invention the polymer composition may comprise a composition as claimed in claim 1 characterized by formulating the drug with a first polymer comprising a repeating molecular unit $—(O—CH_2CH_2—)—_n$, wherein n is 4500 to 5000, and with a second polymer comprising a repeating molecular unit $—(O—CH_2CH_2—)—_n$, wherein n is 6500 to 7500, which first and second polymer carry the drug from the device and release the drug essentially free of polymer retention.

In another aspect of the invention the invention provides a method for treating depressant disorders in a patient in need of antidepressant therapy, wherein the method comprises the step of admitting orally into the patient a dosage form comprising 1 mg to 750 mg of tandospirone that is administered at a rate of release controlled by the dosage form over an extended period up to 24 hours. A further aspect of the invention is to provide a method for admitting into the patient a dosage form comprising 1 mg to 750 mg of tandospirone which method is characterized in that the rate of release of tandospirone versus time up to 24 hours is dosage form controlled tandospirone administration to the patient.

In a particular aspect of the present invention the drug constitutes less than 50% of the composition and in a particular aspect of the invention the polymeric composition comprises:

a. a polymer selected from the repeating molecular unit $—(—O—CH_2—CH_2—)—_n$, wherein n is in the range of 4000 to 5500, and a mixture thereof with a polymer having the same repeating molecular unit wherein n is in the range of 6500 to 7500, b. 0–3% by weight of a lubricant;

c. 0–20% by weight of an osmagent;

d. 0–4% by weight of an antioxidant and e. 0–10% by weight of polyvinyl a binder.

In a further aspect of the invention the applicants have found that when the drug composition is below 45% of the total composition the supply of drug is much improved.

According to a further aspect of the invention there is provided an osmotic delivery device for the delivery of a composition as claimed in any one of the claims, which device comprises:

a. a wall comprising a member selected from cellulose acylate, cellulose diacylate and cellulose triacylate, which wall surrounds:

b. an internal compartment containing the drug composition;

c. at least one passageway in the wall that connects the exterior of the device with the compartment;

d. a push composition in the compartment comprising an osmopolymer that, in the presence of fluid that enters the compartment, increases in dimensions and thereby occupies space in the compartment; and wherein the osmotic device is characterized by e. a drug composition in accordance with the invention which composition delivers the said drug from the device to the patient at a substantially zero order rate of release over a period of 24 hours.

BRIEF DESCRIPTION OF THE DRAWINGS

In these drawing figures, which are not drawn to scale, but are set forth to illustrate various embodiments of the invention, the Figures are as follows.

In the drawing figures and in the specification like parts in related drawing figure are identified by like numbers. The terms appearing earlier in the specification and in the description of the drawings, as well as embodiments thereof, are further described elsewhere in the disclosure.

DETAILED DESCRIPTION OF THE DRAWING FIGURES

Figure 1:
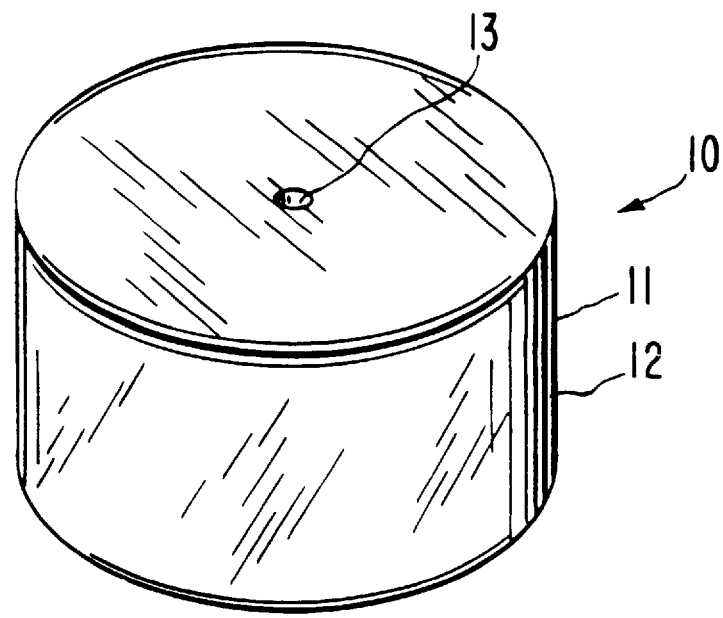
FIG. 1 is a view of a dosage form designed and shaped for administering orally the drugs of formulae (1) and (2) including presently preferred tandospirone to biological, gastrointestinal receptors of drugs of formulae (1) and (2) including tandospirone.

Turning now to the drawing figures in detail, which drawing figures are an example of the dosage forms provided by this invention, and which example is not to be construed as limiting the invention, one example of the dosage form is illustrated in drawing FIG. 1 and designated by the numeral 10. In drawing FIG. 1, dosage form 10 comprises a body member 11 comprising a wall 12 that surrounds and encloses an internal compartment, not seen in drawing FIG. 1. Wall 12 keeps its physical integrity and structure in the presence of osmotic and hydrodynamic pressure generated within dosage form 10 during operation of dosage form 10. Dosage form 10 comprises at least one exit means 13 for connecting the interior of dosage form 10 with the exterior environment of use.

Figure 2:
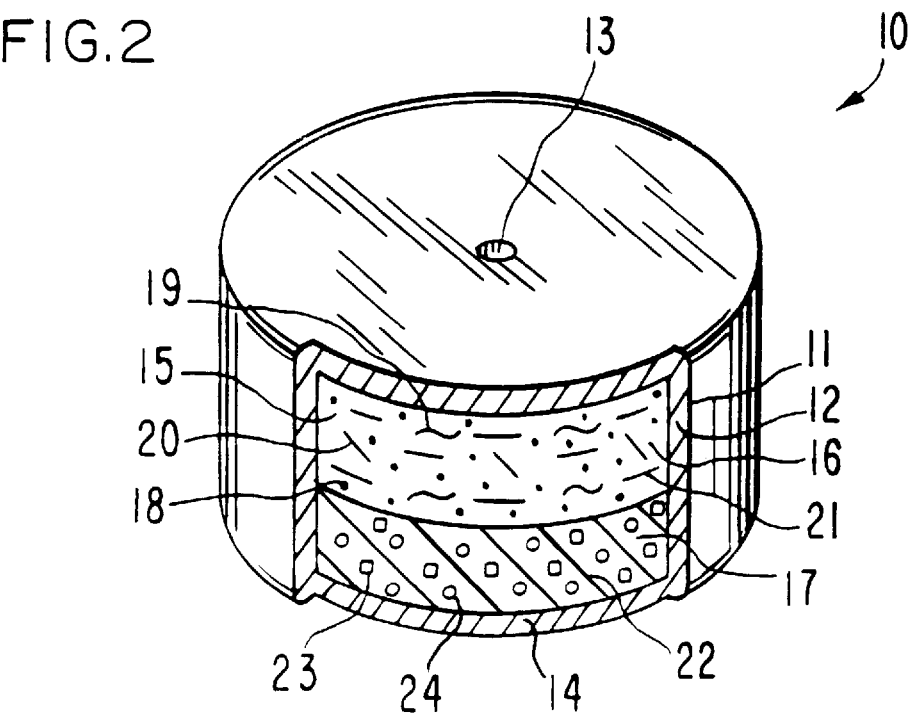
FIG. 2 is an opened-view of the dosage form of drawing FIG. 1, for illustrating the total structure of the dosage form.

In drawing FIG. 2, dosage form 10, manufactured as an osmotic dosage form, is seen in opened view. In drawing FIG. 2, dosage form 10 comprises body 11, wall 12 that is sectioned at 14, depicts wall 12 that surrounds and defines an internal compartment 15. Wall 12 comprises at least one exit means 13 that connects compartment 15 with the exterior of dosage form 10. Dosage form 10 can comprise more than one exit means 13.

Wall 12 of dosage form 10 comprises a composition that is permeable to the passage of an exterior fluid present in the fluid environment of use, and the wall-forming composition is substantially impermeable to the drug of formulae (1) and (2), and to other components present in compartment 15. The composition is semipermeable, it is nontoxic and substantially inert. The composition maintains its physical and chemical integrity, that is, it does not change its chemical nature, independently of the structure of wall 12. Wall 12 comprises from 70 weight percent, (wt %), to 100 wt % of a cellulose wall-forming polymer. The polymer comprises a member selected from the group consisting of cellulose acylate, cellulose diacylate, cellulose triacylate, cellulose acetate, cellulose diacetate and cellulose triacetate. In another operative manufacture, wall 12 comprises additionally from 0 wt % to 25 wt % of a cellulose ether selected from the group consisting of hydroxypropylcellulose and hydroxypropylmethylcellulose; and from 0 wt % to 15 wt % of a polyethylene glycol. The total weight percent of all components comprising wall 12 is equal to 100 wt %.

Dosage form 10, as seen in drawing FIG. 2, in compartment 15 comprises a drug layer 16 and a push layer 17. Drug layer 16 and push layer 17 act together, during operation of dosage form 10, for the delivery of drug of formulae (1) and (2) to a patient in need of formulae (1) and (2) therapy. Drug layer 16 and push layer 17 also act with wall 12 for the controlled rate of release of drug of formulae (1) and (2) over time.

Drug layer 16 comprises 15 wt % to 60 wt % of a drug selected from formula (1) as exemplified by formula (2) which depicts tandospirone, and its therapeutically acceptable salts, identified by dots 18. The therapeutic dose of a formula (1) drug as represented by tandospirone 18 in a single dosage form 10, expressed in milligrams, (mg), is from 1 mg to 750 mg. Individual dosage form 10 comprises 2, 5, 10, 40, 50, 80, 120, 160, 250, 300, 500 and 750 mg of drug for administering in a single dose, or in more than one dose. The pharmaceutically acceptable non-toxic salts of the drugs of formulae (1) and (2) useful for the purpose of the invention include a member selected from the group consisting of inorganic, organic, hydrochloric, hydrobromic, sulfuric, phosphoric, acetic, propionic, butyric, tartaric, citric, maleic, fumaric, lysine, succinic, palmitic, and glycine salts.

Drug layer 16 comprises additionally a polymer 19, depicted by a wavy line, for transporting drug 18 from dosage form 10. Polymer 19, in one manufacture comprises the structure —(O—$CH_2CH_2$—)—$_n$ wherein n is a positive whole number of 4000 to 5500. Representative of the polymer 19 is a poly(oxyethylene) of approximate average molecular weight of $2 \times 10^5$. Polymer 19 in another manufacture comprises the structure (—O—$CH_2CH_2$—)—$_n$ wherein n is a positive whole number of 5700 to 7500. Representative of this polymer 19 is poly(oxyethylene) of approximate average molecular weight of $3 \times 10^5$. Drug layer 16, comprises in another manufacture a polymer composition comprising a first polymer and a second polymer blended together to function as a unit polymer 19 comprising drug 18. The first polymer comprises the polymer described immediately above and the second polymer comprises the second polymer described immediately above. The concentration of polymer 19 in drug layer 16 is in the range of from 20–60 wt %, with the provision that if the drug content is over 45%, polymer 19 should preferably be the first and second polymer pair. The concentration of polymer 19 in drug layer 16 is in the range of from 30–60 wt %, in a more preferred embodiment when the drug content is less than 45% polymer 19 is a single polymer selected from the first polymer. A single poly(ethylene oxide) provides unexpected advantages. For example, a single poly(ethylene oxide) can be used in the drug layer to provide a quicker start-up delivery period for the drug and for delivering more drug in less time. The use of a single poly(ethylene oxide), for example having a molecular weight of 200,000, will hydrate at a faster rate for a quicker start-up and have a lower viscosity for the drug formulation for delivering the drug formulation from the dosage form in a greater cumulative dose in less time. Additionally, for manufacturing purposes, it is more preferred to be able to use a single polymer for delivering the drug whenever possible to achieve this the drug concentrate cannot exceed 45 wt %. For example, in one manufacture of a dosage form provided by the invention comprises 25 wt % to 45 wt % of tandospirone citrate and a single poly(ethylene oxide) comprising a 200,000 molecular weight. Polymer 19, present as a single polymer, or as a first and second polymer pair, effectively transports drug 18 from dosage form 10, and releases drug 18 of formulae (1) or (2) to a drug receptor to produce its therapeutic effect. It is unexpected polymer 19, in both manufactures, can perform its housing-transporting-releasing-compositional functions as a complex drug composition comprising the drug of formulae (1) or (2) essentially-free of any bonding of drug 18 to polymer 19.

Drug layer 16 comprises optionally from zero wt % to 5 wt % of a lubricant 20 such as magnesium stearate or calcium stearate; from 0 to 20 wt % of an osmotically active compound 21 such as a member selected from the group consisting of an inorganic salt, an organic salt, a compound containing an amino group, a carbohydrate, an acid and an ester; and 0 wt % to 4 wt % of an anti-oxidant for imparting stability to the drug composition 16, said anti-oxidant comprising a member selected from the group consisting of ascorbic acid, 2,3-butyl hydroxyanisole, mono-tertiary butyl hydroquinone, and butylated hydroxytoluene; and 0 to 20 wt % of a binder such as polyvinylpyrrolidone (PVP) having a 3,000 to 1,250,000 molecular weight, a cellulose ether such as hydroxypropylmethyl cellulose, or hydroxypropyl cellulose or a sugar such as sorbitol. The total weight percent of all components in drug 16 is equal to 100 wt %.

Second layer 17 comprises 50 wt % to 75 wt % of a polymer 22 comprising the repeating molecular unit —(—O—CH$_2$CH$_2$—)—$_n$, wherein n is a positive whole number of 90,000 to 230,000. Representative of polymer 22 embraced by the repeating molecular unit is a poly(alkaline oxide) comprising poly(ethylene oxide) comprising an approximate average molecular weight of $4\times10^6$ to $10\times10^6$. Polymer 22 provides unexpected operating advantages as the polymer maintains its chemical composition during operation as it imbibes an external aqueous fluid including biological fluid while simultaneously pushing drug layer 16 from dosage form 10 essentially-free of any substantial mixing with drug layer 16. The second layer 17 can be designated as a push layer and it is free of drug. Second layer 17 comprises also 15 wt % to 35 wt % of an osmotically active compound 23, represented by small squares. Representation of osmotically effective compounds comprises salts, esters, carbohydrates and acids, such as a member selected from the group consisting of magnesium sulfate, magnesium chloride, sodium chloride, lithium chloride, potassium sulfate, sodium sulfate, lithium sulfate, potassium chloride, ammonium chloride, potassium lactate, mannitol, urea, inositol, magnesium succinate, tartaric acid, raffinose, sorbitol, sucrose, fructose, glycose and the like. Second layer 17 comprises also 0.1 wt % to 20 wt % of a cellulose ether 24 represented by small circles. Representative of cellulose ethers comprise a member selected from the group consisting of hydroxypropylcellulose and hydroxypropylmethylcellulose having a molecular weight of 9,000 to 22,500. The composition forming push layer 17 also comprises 0 wt % to 5 wt % of a lubricant such as stearic acid, magnesium stearate, calcium stearate, calcium oleate, oleic acid and caprylic acid and 0–4 wt % of an antioxidant selected from those listed above with respect to the drug layer 16. Even though some of the materials noted above, such as the cellulose ethers and sorbitol can also function as a binder, it is often desirable to include from 0–70% of a binder such as PVP, cellulose ethers or sorbitol in the push layer 17. For processing purposes, the layer 17 can optionally contain up to 10% by weight of an inert pigmenting agent such as ferric oxide to impart a color to layer 17 that is different from that of drug layer 16. The poly(oxyethylene) polymers disclosed herein are commercially available from the Union Carbide Corporation, South Charleston, W. Va.

The expression, "exit means 13", as used herein, comprises means and methods suitable for the metered release of the therapeutic drug 18 from compartment 15 of dosage form 10. The exit means 13 comprises at least one passageway, orifice, bore, aperture, pore, porous element, hollow fiber, capillary tube, porous overlay, and porous element that provides for the osmotic controlled release of drug 17. The expression exit means 13 includes a material that erodes or is leached from wall 12 in a fluid environment of use to produce at least one osmotic dimensioned passageway 13 is dosage form 10. Representative materials suitable for forming a passageway, or a multiplicity of passageways comprise a leachable poly(glycolic) acid or poly(lactic) acid polymer in wall 12, a gelatinous filament, poly(vinyl alcohol), leachable polysaccharides, salts and oxides. A pore passageway, or more than one pore passageways can be formed by leaching a leachable compound, such as sorbitol, from wall 12. The passageway possessing controlled release dimensions such as round, triangular, square, elliptical, and the like, for the metered release of drug 17 from dosage form 10. Dosage form 10 can be construed with one or more passageways in spaced apart relationship on a single surface or on more than one surface of dosage form 10. Passageways and equipments for forming passageways are disclosed in U.S. Pat. Nos. 3,845,770; 3,916,899; 4,063,064; 4,088,864 and 4,816,263. Passageways formed by leaching are disclosed in U.S. Pat. Nos. 4,200,098 and 4,285,987.

Dosage form 10, as provided by this invention for administering tandospirone, includes also dosage forms that mediate the efficiency of tandospirone by delivering tandospirone at a rate controlled by the dosage form over an extended time. These dosage forms comprise in addition to the osmotic dosage form comprise a member selected from the group consisting of diffusion, bioerodable, and ion-exchange dosage forms.

The bioerodable dosage form comprises a bioerodable polymer presently in matrix dosage form that provides tandospirone at a release-rate controlled by the bioeroding matrix over time. The bioerodable polymer for forming the dosage form containing tandospirone include poly(ester), poly(amine), poly(lactide), poly(glycolide), poly(lactide-co-glycolide), poly(caprolactone), poly(hydroxybutyric acid), poly(orthoester), poly (orthocarbonate), poly(acetals), poly (peptide), poly(carbohydrate), and poly(dihydropyran).

The diffusion rate-controlled dosage form comprises a diffusion-controlling polymer through which the tandospirone is released by diffusion. The tandospirone diffusion can be through the polymer or through a porous-polymer membrane. The diffusion dosage form structurally includes a polymer matrix that is a tandospirone reservoir or through a contacting polymer rate-governing membrane. Representative of polymers for proving diffusional dosage forms comprise a member selected from the group consisting of poly(olefin), poly(vinyl), poly(carbohydrate), poly (peptide), poly(condensation), poly(rubber), and poly (silicon). Representative of specific polymers consists of a member selected from the group consisting of poly (ethylene), poly(propylene), copoly(ethylene-vinyl acetate), poly(isobutylethylene), poly(vinylautate), cross-linked poly (vinylalcohol), poly(methacrylate), poly(amide), poly (ester), and poly(silicone).

The dosage form comprising an ion-exchange activity comprises a water-insoluble crosslinked polymer with tandospirone bound to the ion-exchange resin. The tandospirone is released at a rate controlled by the tandospirone-resin complex by the ionic environment within the gastrointestinal tract. The ion-exchange resins that can be adapted for the manufacture of the dosage form comprise a cation-exchange resin and an anion-exchange resin. The cation-exchange resins include strong-acid and weak-acid resins as with sulfonic acid, carboxylic acid and phosphonic acid and the anion-exchange resins include strong-base and weak-base resins as with quaternary ammonium, secondary amine, tertiary amine aromatic and tertiary amine aliphatic resins. So specific examples of ion-exchange resins mention is made of acidic ion-exchange resins such as Amberlite IR-120, basic ion-exchange resins such as Amberlite IRA-400, and weak basic ion-exchange resins such as Amberlite IR-45.

DESCRIPTION OF PROCESSES FOR MANUFACTURING THE DOSAGE FORM OF THE INVENTION

Wall 12 of osmotic dosage form 10 can be formed in one technique using the air suspension procedure. This procedure consists in suspending and tumbling the compressed layers in a current of air and wall forming composition until a wall is applied to the drug forming compartment. The air suspensions procedure is well-suited for independently forming the wall. The air suspension procedure is described in U.S. Pat. No. 2,799,241; *J. Am. Pharm. Assoc.,* Vol. 48, pages 451 to 459, 1959; and ibid. Vol. 49, pages 82 to 84, 1960. Osmotic dosage forms can also be coated with a wall-forming composition in a Wurster® air suspension coater, using acetone-water cosolvent, 90:10, wt:wt, using 2.5 to 7 wt % polymer solids. The Aeromatic® air suspension coater using a methylene dichloride methanol cosolvent, 87:13, v:v, also can be used for applying the wall. Other wall forming techniques, such as pan coating, can be used for providing the dosage form. In the pan coating system, wall forming compositions are deposited by successive spraying of the composition on the bilayered compartment, accompanying by tumbling in a rotating pan. A larger volume of cosolvent can be used to reduce the concentration of polymer solids to produce a thinner wall. Finally, the wall coated compartments are laser or mechanically drilled and dried in a forced air or humidity oven for a week to free the dosage form of solvent. Generally, the walls formed by these techniques have a thickness of 2 to 20 mils (0.051 to 0.51 mm) with a presently preferred thickness of 2 to 6 mils (0.051 to 0.15 mm).

Dosage form 10 of the invention is manufactured by standard manufacturing techniques. For example, in one manufacture, the beneficial drug and other ingredients comprising the first layer facing the exit means are blended and pressed into a solid layer. The drug and other ingredients can be blended also with a solvent and mixed into a solid or semisolid formed by conventional methods such as ball-milling, calendering, stirring or rollmilling and then pressed into a preselected shape. The layer possesses dimensions that correspond to the internal dimensions of the area the layer is to occupy in the dosage form and it also possesses dimensions corresponding to the second layer for forming a contacting arrangement therewith. Next, the osmopolymer layer is placed in contact with the drug layer. The layering of the drug layer and the osmopolymer layer can be fabricated by conventional press-layering techniques. Finally, the two layer compartment forming members are surrounded and coated with an outer wall. A passageway is laser drilled through the wall to contact the drug layer, with the dosage form optically oriented automatically by the laser equipment for forming the passageway on the preselected surface.

In another manufacture, dosage form 10 is manufactured by the wet granulation technique. In the wet granulation technique, the drug and the ingredients comprising the first layer are blended using an organic or inorganic solvent, such as isopropyl alcohol-methylene dichloride 80/20 v/v as the granulation fluid. Other granulating fluid, such as water or denatured alcohol 100%, can be used for this purpose. The ingredients forming the first layer are individually passed through a 40 mesh screen and then thoroughly blended in a mixer. Next, other ingredients comprising the first layer are dissolved in a portion of the granulation fluid, such as the cosolvent described above. Then, the latter prepared wet blend is slowly added to the drug blend with continual mixing in the blender. The granulating fluid is added until a wet blend is produced, which wet mass then is forced through a 20 mesh screen onto oven trays. The blend is dried for 18 to 24 hours at 25° C. to 40° C. The dry granules are screened then with a 16 mesh screen. Next, a lubricant is passed through an 60 mesh screen and added to the dry screened granule blend. The granulation is put into milling jars and mixed on a jar mill for 2 to 10 minutes. The first and second layer compositions are pressed into a layered tablet, for example, in a Manesty® layer press.

Another manufacturing process that can be used for providing the drug and push composition comprises blending the powdered ingredients in a fluid bed granulator. After the powdered ingredients are dry blended in the granulator, a granulating fluid, for example poly(vinyl-pyrrolidone) in water, is sprayed onto the powders. The coated powders are then dried in a granulator. This process coats-agglomerates all the ingredients present therein while spraying the granulating fluid. After the granules are dried, a lubricant such as stearic acid or magnesium stearate is blended as above into the mixture. The granules are pressed then in the manner described above.

We have found that when the fluid bed granulating process is employed to manufacture the push layer 17, the antioxidant (BHT) that is initially included in the polyoxyethylene by the manufacturer, is removed during processing. It therefore becomes necessary to add additional antioxidant to the formulation and this addition can be accomplished during the fluid bed granulation as described in more detail in Example 9.

The osmotic device of this invention is manufactured in another embodiment by mixing a drug with composition forming ingredients and pressing the composition into a solid layer possessing dimensions that correspond to the internal dimensions of the compartment space adjacent to a passageway. In another embodiment, the drug and other first composition forming ingredients and a solvent are mixed into a solid, or a semi-solid, by conventional methods such as ballmilling, calendaring, stirring or rollmilling, and then pressed into a preselected layer forming shape.

In the manufactures as presented above, the manufacture comprising a layer of a composition comprising an osmopolymer and an optional osmagent are placed in contact with the layer comprising the drug, and the two lamina comprising the layers are surrounded with a semipermeable wall. The layering of the first drug composition and the second osmopolymer optional osmagent composition can be accomplished by using a conventional two-layer tablet press technique. The wall can be applied by molding, spraying or dipping the pressed shapes into wall forming materials. Another and presently preferred technique that can be used for applying the wall is the air suspension coating procedure. This procedure consists in suspending and tumbling the two layers in a current of air until the wall forming composition surrounds the layers. The air suspension procedure is described in U.S. Pat. No. 2,799,241; *J. Am. Pharm. Assoc.,* Vol. 48, pp 451–459 (1979); and, ibid, Vol. 49, pp 82–84 (1960). Other standard manufacturing procedures are described in *Modern Plastics Encyclopedia,* Vol. 46, pp 62–70 (1969); and in *Pharmaceutical Science,* by Remington, 14th Ed., pp 1626–1979, (1970), published by Mack Publishing Co., Easton, Pa. The dosage forms can be manufactured by following the teaching in U.S. Pat. Nos. 4,327,725; 4,612,008; 4,783,337; 4,863,456; and 4,902,514.

Exemplary solvents suitable for manufacturing the wall, the laminates and laminae include inert inorganic and organic solvents that do not adversely harm the materials and the final wall of the final laminated wall. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptaene, ethylene glycol monoethyl ether, ethylene glycol monoethylacetate, methylene dichloride, ethylene dichloride, propylene dichloride, carbon chloroform, nitroethane, nitropropane, tetrachloroethane, ethyl ether, isopropyl ether, cyclohexane, cycl-octane, toluene, naphtha, 1,4-dioxane, tetrahydrofuran, diglyme, aqueous and non-aqueous mixtures thereof, such as acetone and water, acetone and methanol, acetone and ethyl alcohol, methylene dichloride and methanol, and ethylene dichloride and methanol.

DETAILED DISCLOSURE OF EXAMPLES PROVIDED BY THE INVENTION

The following examples are merely illustrative of the present invention and they should not be considered as limiting the scope of the invention in any way as these examples and other equivalents thereof will become apparent to those versed in the art in the light of the present disclosure, the drawings and the accompanying claims.

EXAMPLE 1

A dosage form adapted, designed and shaped as an osmotic drug delivery device is manufactured as follows: first, 12.5 kg of micronized tandospirone citrate, 5.62 kg of poly(ethylene oxide) possessing a 200,000 molecular weight and 5.62 kg of a poly(ethylene oxide) possessing a 300,000 molecular weight are added to a Freund Flo-Coater's® bowl, a fluid bed granulator. The bowl was attached to the coater and granulation process was initiated for effecting granulation. Next, the dry powders were air suspended and mixed for 7 minutes. Then, a solution prepared by dissolving 1000 g of poly(vinylpyrrolidone) identified as K29-32 having an average molecular weight of 40,000, in 15,667 g of water was sprayed from 3 nozzles onto the powder. The coating conditions were monitored during the process of aqueous poly(vinylpyrrolidone) as follows: solution spray rate of 125 g/min from each nozzle for a total spray rate of 375 g/min; inlet temperature 45° C.; and process air flow of 1000 cfm.

The coating process was computerized and automated in cycles. Each cycle contained 30 seconds of solution spraying followed by two seconds of drying and 10 seconds of filter bags shaking to unglue and possible powder deposits. At the end of the solution spraying, 16,667 g, the coated granulated particles were continued with the drying process for 25 minutes. The machine was turned off, and the coated granules were removed from the Flo-Coater. The coated granules were sized using a Fluid Air Mill. The granulation was transferred to a Rotocone®, mixed and lubricated with 250 g of magnesium stearate and mixed with 12.5 g of butylated hydroxytoluene.

Next, a push composition is prepared as follows: first, 415.5 g of pharmaceutically acceptable poly(ethylene oxide) comprising a 7,500,000 molecular weight, 150 g of sodium chloride and 6 g of ferric oxide separately are screened through a 40 mesh screen. Then, all the screened ingredients are mixed with 30 g of hydroxypropylmethylcellulose comprising a 11,200 molecular weight to produce a homogeneous blend. Next, 300 mg of denatured anhydrous alcohol is added slowly to the blend with continuous mixing for 5 minutes. The freshly prepared wet granulation is passed through a 20 mesh screen, allowed to dry at room temperature for 16 hours, and again passed through a 20 mesh screen. The screened granulation is mixed with 1.5 g of magnesium stearate in a rollermill for 5 minutes.

Next, the tandospirone drug composition and the push composition are compressed into bilayered tablets. First, 352 mg of the tandospirone composition is added to a punch and tamped, then, 175 mg of the push composition is added and the layers are pressed under a pressure head of two tons into a 7/16" (1.11 cm) diameter contacting layered arrangement.

The bilayered arrangements are coated with a semipermeable wall. The wall forming composition comprises 95% cellulose acetate having a 39.8% acetyl content, and 5% polyethylene glycol having a molecular weight of 3350. The wall-forming composition is dissolved in an acetone:water (90:10 wt:wt) cosolvent to make a 4% solids solution. The wall forming composition is sprayed onto and around the bilayers in a 24" Vector Hi-Coater.

Next, two 25 mil (0.635 mm) exit passageways are mechanically drilled through the semipermeable wall to connect the drug layer with the exterior of the dosage system. The residual solvent is removed by drying for 48 hours at 50° C. and 50% humidity. Next, the osmotic systems are dried for 1 hour at 50° C. to remove excess moisture. The dosage form produced by this manufacture provides 50 wt % tandospirone citrate, 45 wt % poly (ethylene oxide) possessing a blend 200,000 molecular weight and a 300,000 molecular weight, 4 wt % poly(vinyl pyrrolidone) possessing a 40,000 molecular weight, 0.95 wt % magnesium stearate, and 0.05 wt % butyl hydroxytoluene.

Figure 3A:
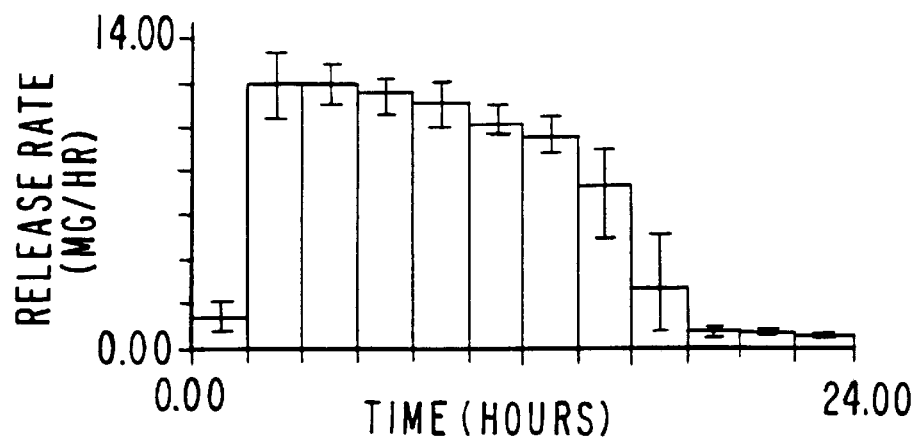
FIGS. 3A and 3B are graphs that depict the dose of tandospirone citrate released per hour over a prolonged period of twenty-four hours and the cumulative dose released from the dosage form.
Figure 3B:
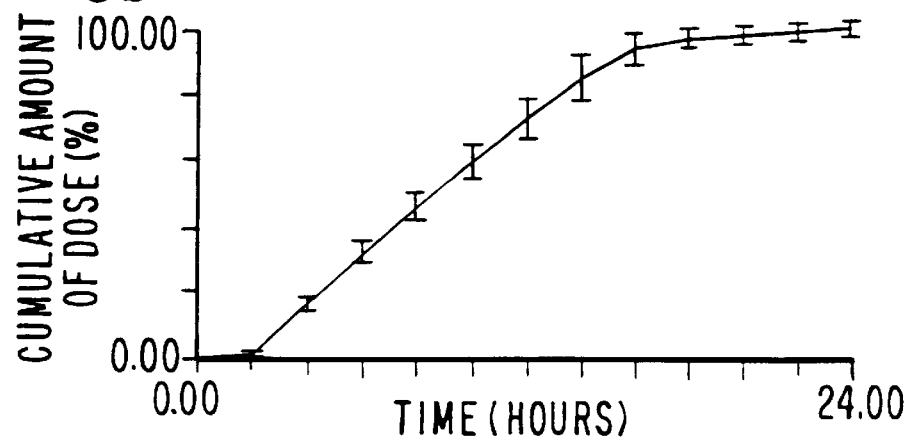

The push composition comprises 68.8 wt % poly(ethylene oxide) comprising a 7,500,000 molecular weight, 25 wt % sodium chloride, 5 wt % hydroxypropylmethylcellulose possessing 11,200 molecular weight, 1.0 wt % ferric oxide and 0.2 wt % magnesium stearate. The semipermeable wall comprises 95 wt % cellulose acetate comprising a 39.8% acetyl content, and 5.0 wt % polyethylene glycol comprising a 3350 molecular weight. The dosage form comprises two passageways, 25 mils (0.635 mm), and it had a tandospirone citrate mean release rate of 11.67 mg/hr. Accompanying FIGS. 3a and 3b depict the delivery pattern for a dosage form provided by this example.

EXAMPLE 2

Figure 4:
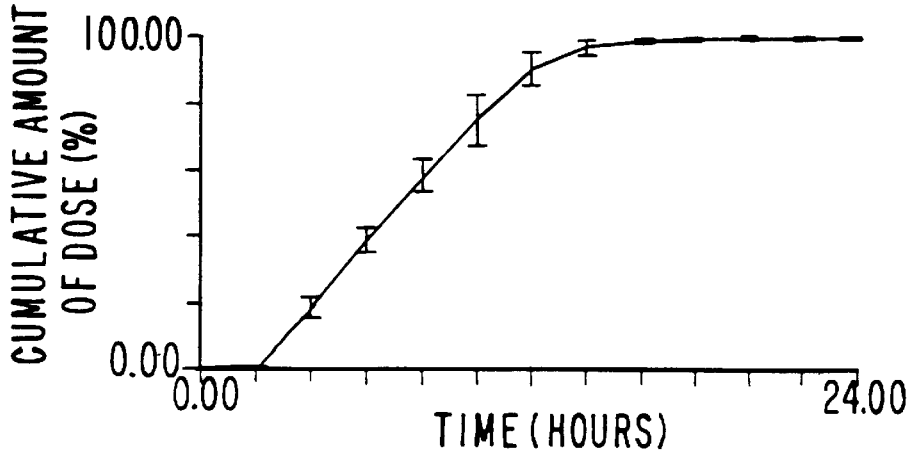
FIG. 4 is a graph depicting the cumulative amount of tandospirone citrate released at a controlled rate from a different dosage form provided by the invention.

Following the procedure of Example 1, an osmotic dosage form comprising a drug dose of 80 mg of drug was prepared to provide the following dosage form: a drug layer comprising 50 wt % of tandospirone citrate, 25 wt % of poly(ethylene oxide) comprising a 200,000 molecular weight, 19.95 wt % of poly(ethylene oxide) comprising a 300,000 molecular weight, 4.0 wt % of poly(vinyl pyrrolidone), 0.05 wt % of butyl hydroxytoluene, and 1.0 wt % magnesium stearate. The push composition comprises 68.75 wt % poly(ethylene oxide) of 7,500,000 molecular weight, 25.0 wt % sodium chloride, 5.0 wt % hydroxypropylmethylcellulose, 1 wt % ferric oxide and 0.25 wt % magnesium stearate. The wall comprises 95 wt % cellulose acetate comprising 39.8% acetyl content and 5 wt % poly(ethylene glycol) of 3350 molecular weight. The dosage form comprises two 30 mils orifices, 0.762 m, and the cumulative release rate is depicted in FIG. 4. In this example, the drug layer weighed 176 mg, consisting of a dose or 80 mg of tandospirone citrate plus an overage of 8 mg tandospirone citrate.

EXAMPLE 3

The procedures of Example 1 and Example 2 are followed in this example to provide a dosage form comprising a total drug content of 132 mg of tandospirone citrate forming a tandospirone citrate dose of 120 mg and an overage of 12 mg. exhibiting a mean release rate of 9.17 mg/hr of tandospirone citrate over a 15.6 hour period of time. In this example, the total weight of the drug layer was 264 mg, the total weight of the push layer was 130 mg, the dosage form had a diameter of 13/32 inches (10.32 mm) and 2 orifices of 30 mils (0.762 mm).

EXAMPLE 4

A dosage form is provided comprising the following: a total tandospirone citrate of 88 mg forming a drug dose of tandospirone of 80 mg and an 8 mg overage; a drug layer comprising 50 wt % tandospirone citrate, 70 wt % poly(ethylene oxide) comprising a blend of an average 200,000 molecular weight, and an average 300,000 molecular weight 4 wt % poly(vinyl pyrrolidone) of 40,000 average molecular weight, 0.95 wt % magnesium stearate, and 0.05 wt % butyl hydroxytoluene; the push layer weighed 174 mg and comprises 68.75 wt % poly(ethylene oxide) of 7,500,000 molecular weight, 25 wt % sodium chloride, 6 wt % hydroxypropylmethylcellulose, 1 wt % ferric oxide, and 0.25 wt % magnesium stearate; a wall comprising 95 wt % cellulose acetate comprising an acetyl content of 39.8%, and 5 wt % polyethylene glycol. The dosage form comprises two 25 mils (0.635 mm) passageways, and a nominal $T_{90}$ over 14 hours means release rate of 6.1 mg/hr of tandospirone citrate.

EXAMPLES 5 AND 6

Two dosage forms comprising a total dose of 176 mg of tandospirone citrate were prepared wherein both dosage forms comprised a 352 mg drug layer comprising 50 wt % tandospirone citrate, 33.75 wt % of poly(ethylene oxide) comprising a 200,000 molecular weight, 11.25 wt % of poly(ethylene oxide) comprising a 300,000 molecular weight, 4 wt % of poly(vinyl pyrrolidone) comprising 40,000 molecular weight, and 1 wt % magnesium stearate. The push layer was as described in Example 4. One dosage form provided by this example comprises one passageway of 25 mils diameter (0.635 mm) and a nominal $T_{90}$ mean release rate of 10.820 mg/hr for 15.7 hours; and the other dosage form comprises two passageways of 25 mils diameter (0.635 mm), a nominal $T_{90}$, and a mean release rate of 11.128 mg/hr for 15 hours.

EXAMPLES 7 AND 8

Figure 5:
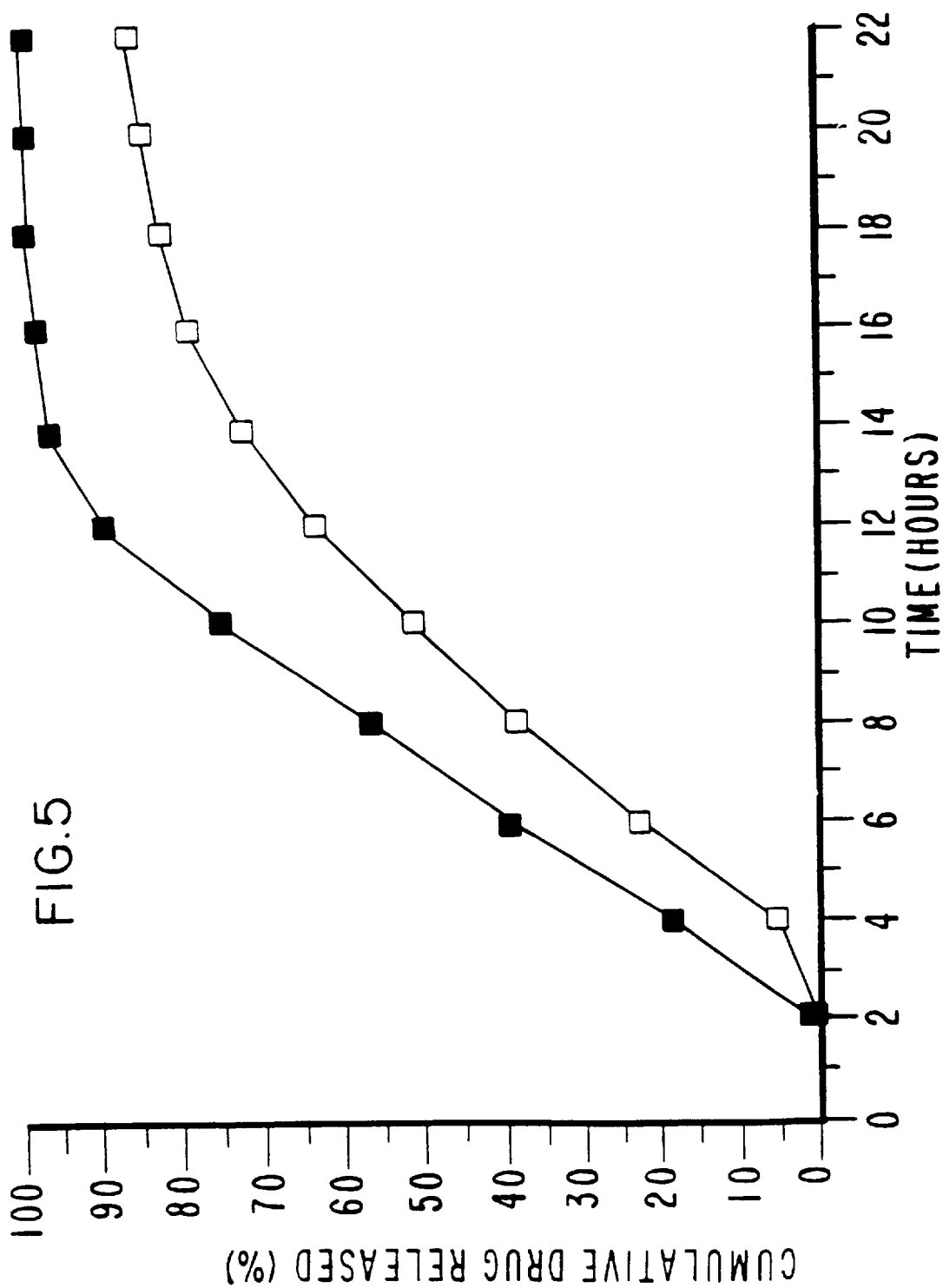
FIG. 5 is a graph depicting the release from two different dosage forms comprising different drug layers from the dosage forms.

Two dosage forms were manufactured comprising a drug layer weighing 352 mg and a push layer weighing 174 mg. The drug layer in one manufacture comprises 50 wt % tandospirone citrate, 25 wt % poly(ethylene oxide) comprising a 200,000 molecular weight, 19.95 wt % poly(ethylene oxide) comprising a 300,000 molecular weight, 4 wt % hydroxypropylmethylcellulose comprising a 11,200 molecular weight, 1 wt % magnesium stearate and 0.05 wt % of butyl hydroxytoluene. The drug layer in the other manufacture comprises 50 wt % tandospirone citrate, 25 wt % poly(ethylene oxide) comprising a 200,000 molecular weight, 19.95 wt % of poly(ethylene oxide) comprising a 300,000 molecular weight, 4 wt % poly(vinyl pyrrolidone), comprising a 40,000 molecular weight, 1 wt % magnesium stearate and 0.05 wt % butyl hydroxytoluene. The push layer in both manufactures comprises 68.75 wt % poly(ethylene oxide) comprising a 7,300,000 molecular weight, 25.00 wt % sodium or potassium chloride, 5 wt % hydroxypropylmethylcellulose comprising a 17,875 molecular weight, 1.00 wt % ferric oxide and 0.25 wt % magnesium stearate. The semipermeable wall, in both manufactures, comprises 95 wt % cellulose triacetate consisting of 39.8% acetyl content and 5 wt % poly(ethylene glycol) of 3350 molecular weight. The dosage form comprises two 25 mil (0.635 mm) passageways connecting the drug layer with the exterior of the dosage form. Accompanying drawing FIG. 5 depicts the drug release over time. The dark square denotes a drug layer comprising poly(vinyl pyrrolidone) and the plain squares denote a drug layer comprising hydroxypropylmethylcellulose.

EXAMPLE 9

A dosage form adapted, designed and shaped as an osmotic drug delivery device is manufactured as follows: first, 9.675 kg of micronized tandospirone citrate, 14.575 kg of poly(ethylene oxide) possessing a 190,000 to 210,000 molecular weight with an average 200,000 molecular weight are added to a Freund Flo-Coater's® bowl, a fluid bed granulator. The granulation process was initiated for effecting granulation. Next, the dry powders were air suspended and mixed for 4 minutes. Then a solution prepared by dissolving 500 g of poly(vinylpyrrolidone) identified as K29-32 having an average molecular weight of 40,000 in 7,850 g of water was sprayed from 3 nozzles onto the powder. The coating conditions were monitored during the process of aqueous poly (vinylpyrrolidone) as follows; solution spray rate of 110 g/min from each nozzle for a total spray rate of 330 g/min; inlet temperature 45° C.; and process air flow of 1000 cfm.

The coating process was computerized and automated in cycles. Each cycle contained 30 seconds of solution spraying followed by two seconds of drying and 10 seconds of filter bags shaking to unglue any possible powder deposits. At the end of the solution spraying the coated particles were further dried by the drying process for 25 minutes. The machine was turned off, and the coated granules were removed from the Flo-Coater. The coated tandospirone were sized using a Fluid Air Mill. The particles were transferred to a Rotocone®, lubricated and mixed with 237.5 g of magnesium stearate and mixed with 12.5 g of butylated hydroxytoluene.

Next the push composition is prepared as follows: first, 36,000.0 grams of sodium chloride, and 1,200.0 grams of red ferric oxide are separately screened through an 8 mesh screen using the Quadro-Co Mill. Then the screened ingredients plus 76,410 grams of pharmaceutical acceptable poly (ethylene oxide) comprising of 7,500,000 molecular weight, and 2,090 grams of hydroxypropylmethylcellulose comprising 11,200 molecular weight are dispensed into the bowl of the 120 kg Glatt fluid bed machine. Next, the dry powders are air suspended and mixed for 3 minutes. To prepare the binder solution, first, 3,910.0 grams of hydroxypropylmethylcellulose comprising 11,200 molecular weight is dissolved in 45,339 grams of water, and 90.0 grams of butylated hydroxy toluene is dissolved in 650 grams of denatured ethanol. The two solutions are combined to form the final binder solution. The condition monitored during the process are as follows: solution spray rate of 800 g/min (3 nozzles are used); inlet temperature 45° C.; outlet temperature 24° C., and process air flow of 3,000 ft$^3$/min. The blending process is computerized and automatic in cycles. Each cycle contains 1.5 minutes of solution spraying followed by 10 seconds of bag shaking to remove any possible powder deposits. A total of 44,000 grams of solution is sprayed. After solution spaying, the particles are dried for 50 minutes at 21° C. to reach a moisture content of 0.29%. The drug particles are removed and sized through an 8 mesh screen using the Quadro-Co Mill. Then 300.0 grams of magnesium stearate, screened through a 16 mesh screen, is mixed into the granulation using a tote tumbler for 3 minutes at 8 rpm.

Next, the tandospirone citrate drug composition and the push composition are compressed into bilayered tablets. First, 434 mg of the tandospirone containing composition is added to a punch and tamped, then 260 mg of the push composition is added and the layers are pressed under a pressure head of two tons into a 0.700×0.375" (1.778×0.953 cm) modified oval contacting layered arrangement.

The bilayered arrangements are coated with a semipermeable wall. The wall forming composition comprises 95% cellulose acetate having a 39.8% acetyl content, and 5% polyethylene glycol having a molecular weight of 3350. The wall-forming composition is dissolved in an acetone:water (95:5 wt:wt) cosolvent to make a 4% solids solution. The wall forming composition is sprayed onto and around the bilayers in a 24" (60 cm) Vector Hi-Coater.

Figure 6A:
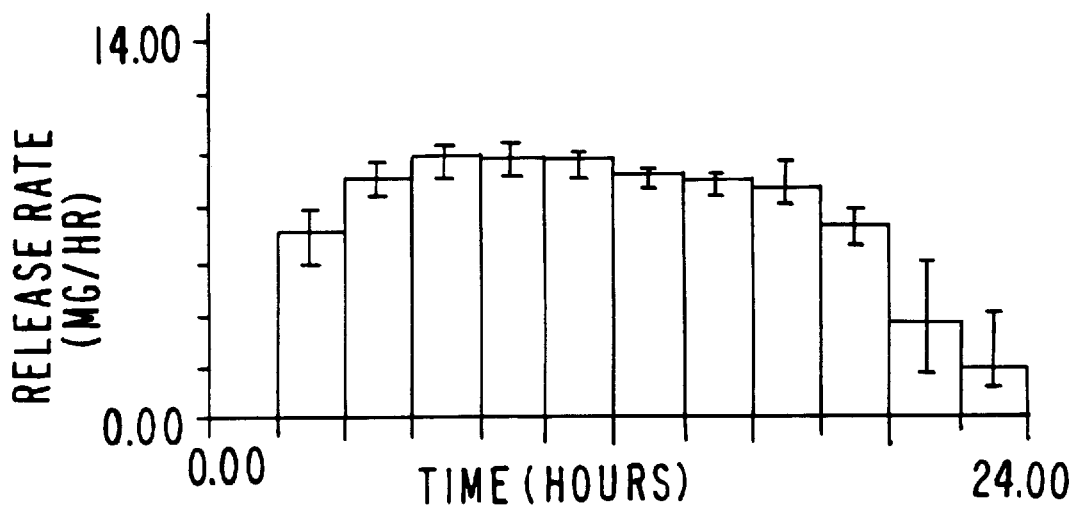
FIGS. 6A and 6B are graphs depicting the pattern of tandospirone citrate release from a preferred embodiment of this invention; and, FIGS. 7A and 7B are graphs depicting the performance of two different tandospirone citrate containing continuous extended release dosage forms.
Figure 6B:
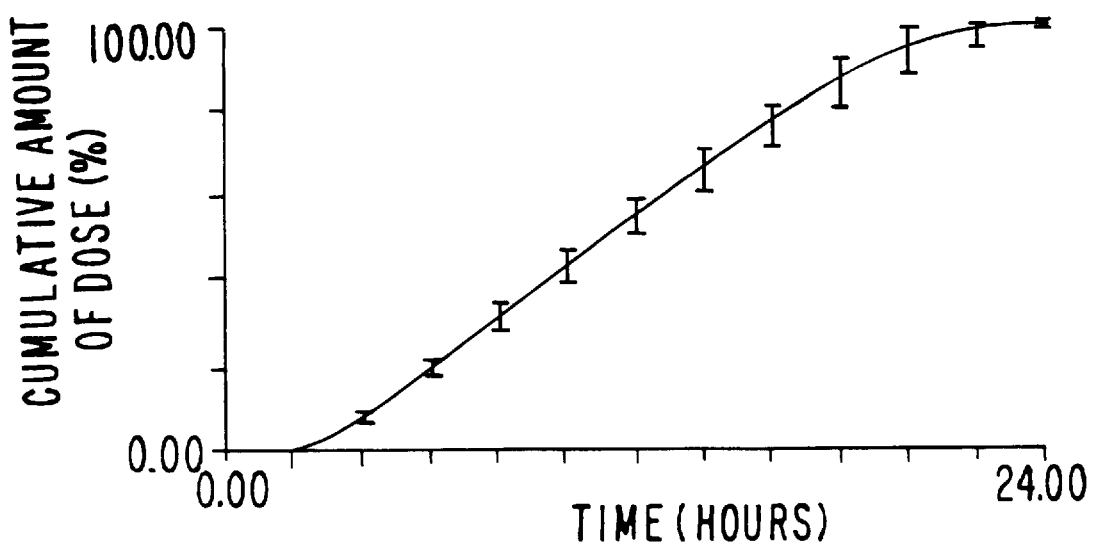

Next, one 25 mil (0.635 mm) exit passageway is laser drilled through the semipermeable wall to connect the drug layer with the exterior of the dosage system. The residual solvent is removed by drying for 48 hours at 50° C. and 50% humidity. Next, the osmotic systems are dried for 1 hour at 50° C. to remove excess moisture. The dosage form produced by this manufacture provides 38.70 wt % tandospirone citrate, 58.30 wt % poly(ethylene oxide) possessing a 200,000 molecular weight, 2.00 wt % poly(vinyl pyrrolidone) possessing a 40,000 molecular weight, 0.95 wt % magnesium stearate, and 0.05 wt % butyl hydroxytoluene in drug composition. The push composition comprises 63.675 wt % poly(ethylene oxide) comprising a 7,500,000 molecular weight, 30.00 wt % sodium chloride, 5 wt % hydroxypropylmethylcellulose possessing 11,200 molecular weight, 1.0 wt % ferric oxide, 0.25 wt % magnesium stearate and 0.075 wt % BHT, (butylhydoxytoluene). The semipermeable wall comprises 95 wt % cellulose acetate comprising a 39.8% acetyl content, and 5.0 wt % polyethylene glycol comprising a 3350 molecular weight. The dosage form comprises one passageway, 25 mils (0.635 mm), and it had a tandospirone citrate mean release rate of 10.5 mg/hr. The delivery pattern is shown in FIGS. 6A and 6B which is characterized by a substantially constant release rate from about hour 4 to hour 20 followed by a rapid termination of delivery.

EXAMPLE 9A

The procedure of Example 9 is followed with all conditions as set forth, except the poly(ethylene oxide) in the drug layer possessed a 290,000 to 310,000 molecular weight with an average of 300,000 molecular weight and possesses two exit ports.

EXAMPLE 10

A dosage form is provided for delivering a tandospirone citrate drug sublingually, wherein the dosage form is sized, shaped and adapted for sublingual, that is subglossal below or beneath the tongue for administering the drug to the hypoglossal drug receptors. The sublingual dosage form for administering tandospirone citrate to the sublingual tandospirone receiving area to a patient in need of tandospirone therapy, comprises: (a) a wall comprising a member selected from the group consisting of cellulose acylate, cellulose diacylate, cellulose triacylate, cellulose acetate, cellulose diacetate and cellulose triacetate, which semipermeable wall surrounds; (b) an internal lumen; with (c) at least one exit passageway in the wall that connects the exterior of the sublingual dosage form with the lumen; (d) a push layer in the lumen comprising an osmotic agent, that in the presence of fluid that enters the lumen increases in volume and thereby occupies space in the lumen; and, (e) a tandospirone layer in the lumen initially separate from the push layer and in initial contact with the push layer, which tandospirone layer comprises a poly(oxyethylene) comprising a $1.75\times10^5$ to $2.25\times10^5$ molecular weight (n=4,000 and 5500 respectively) and a poly(oxyethylene) comprising a $2.50\times10^5$ to $3.25\times10^5$ molecular weight (n=5700 and 7500 respectively) which dosage form delivers the tandospirone composition through the exit to the patient at a substantially zero order rate of release over a period of up to 24 hours to product a tandospirone plasma level for treating depressive disorders, including major depression that is single or recurrent, bipolar disorders such as depressive disorders, dysthymia, major depression with or without melancholia, or cyclothymia as characterized by alternate lively and depressed moods.

EXAMPLE 11

A dosage form is provided for delivering tandospirone citrate buccally, comprising the area adjacent to, or in the direction of the check, which dosage form is sized, shaped and adapted for positioning in the buccal area of the mouth for administering tandospirone to buccal tandospirone drug receptor areas, wherein the tandospirone buccal dosage form comprises: (a) a wall comprising a member selected from the group consisting of cellulose acylate, cellulose diacylate, cellulose triacylate, cellulose acetate, cellulose diacetate and cellulose triacetate, which buccally acceptable semipermeable wall surrounds: (b) an internal lumen; with (c) at lease one exit passageway in the wall that connects the buccal exterior with the interior lumen of the buccal dosage form; (d) a push layer in the lumen comprising an osmotic agent, that in the presence of buccal fluid that enters the lumen increases in volume and thereby occupies space in the lumen; and (e) a tandospirone layer in the lumen initially separated from the push layer and in initial contact with the push layer, which tandospirone layer comprises a poly(O—CH$_2$CH$^2$)$^n$ wherein n is 4,000 to 5,500 and a second and different poly(O—CH$_2$CH$^2$)$^n$ wherein n is 5,700 to 7,500, which buccal dosage dorm delivers the tandospirone composition through the exit to the patient at a substantially zero order rate of drug delivery over a period up to 24 hours to produce a tandospirone plasma level for treating depressive disorders including major depression that is single or recurrent, bipolar disorders such as depressive disorders, dysthymia, major depression with or without melancholia, or cyclothymia as characterized by alternate lively and depressed moods.

EXAMPLE 12

A dosage form comprising 160 mg of tandospirone citrate is made as follows: first, 12.5 kg of tandospirone citrate is blended with 2.813 kg of poly(ethylene oxide) having a 200,000 molecular weight and 8.438 kg of poly(ethylene oxide) having a 300,000 molecular weight and added to a fluid bed granulator bowl. The granulation was initiated to effect granulation of the tandospirone citrate/poly(ethylene oxide). Next, the granules were dried by air suspension for 3 minutes. Then, a solution prepared by dissolving 500 g of poly(vinylpyrrolidone) possessing a 40,000 molecular weight in 7,850 g of distilled water was sprayed from 3 nozzles onto the power. The coating conditions were monitored during the process of the aqueous poly(vinylpyrrolidone) as follows: a solution spray rate of 125 g/min from each nozzle for a total spray rate of 375 g/min; an inlet temperature of 45° C.; and an air flow of 1000 cfm.

The coating process was computerized and automated in cycles. Each cycle contained 30 seconds of solution spraying followed by two seconds of drying and 10 seconds of filter bags shaking to unglue and possible powder deposits. At the end of the solution spraying the coated granulated particles were continued with the drying process for 25 minutes. The is machine was turned off, and the coated granules were removed from the Flo-Coater. The coated granules were sized using a Fluid Air Mill. The granulation was transferred to a Rotocone®, mixed and lubricated with 245 g of magnesium stearate and mixed with 12.5 g of butylated hydroxytoluene.

Next, a push composition is prepared as follows: first, 415.5 g of pharmaceutically acceptable poly(ethylene oxide) comprising a 7,500,000 molecular weight, 150 g of sodium chloride and 6 g of ferric oxide separately are screened through a 40 mesh screen. Then, all the screened ingredients are mixed with 30 g of hydroxypropylmethylcellulose comprising a 11,200 molecular weight to produce a homogeneous blend. Next, 300 mg of denatured anhydrous alcohol is added slowly to the blend with continuous mixing for 5 minutes. The freshly prepared wet granulation is passed through a 20 mesh screen, allowed to dry at room temperature for 16 hours, and again passed through a 20 mesh screen. The screened granulation is mixed with 1.5 g of magnesium stearate in a rollermill for 5 minutes.

Next, the tandospirone citrate composition and the push composition are compressed into bilayered tablets. First, 352 mg of the tandospirone composition is added to a punch and tamped, then 175 mg of the push composition is added and the layers are pressed under a pressure head of two tons into a 7⁄16" (1.11 cm) diameter contacting layered arrangement.

The bilayered arrangements are coated with a semipermeable wall. The wall forming composition comprises 95% cellulose acetate having a 39.8% acetyl content, and 5% polyethylene glycol having a molecular weight of 3350. The wall-forming composition is dissolved in an acetone:water (95:5 wt:wt) cosolvent to make a 4% solids solution. The wall forming composition is sprayed onto and around the bilayers in a 24" (60 cm) Vector Hi-Coater.

Figure 7A:
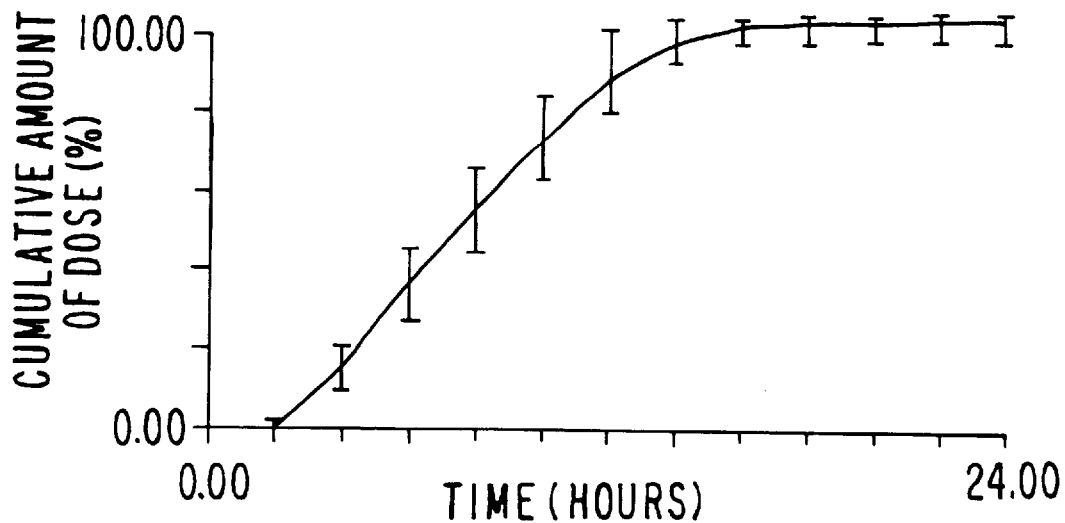

Next, two 25 mil (0.635 mm) exit passageways are mechanically drilled through the semipermeable wall to connect the drug layer with the exterior of the dosage form. The residual solvent is removed by drying for 48 hours at 50° C. and 50% humidity. Next, the osmotic dosage form is dried for 1 hour at 50° C. to remove excess moisture. The dosage form produced by this manufacture provided 50 wt % tandospirone citrate, 11.25 wt % poly(ethylene oxide) having a 200,000 molecular weight, 33.75 wt % poly(ethylene oxide) having a 300,000 molecular weight, 4 wt % poly(vinyl pyrrolidone) possessing a 40,000 molecular weight, 1.0 wt % magnesium stearate, and 0.05 wt % butyl hydroxytoluene. The push composition comprises 68.8 wt % poly(ethylene oxide) comprising a 7,500,000 molecular weight, 25 wt % sodium chloride, 5 wt % hydroxypropylmethylcellulose possessing 11,200 molecular weight, 1.0 wt % ferric oxide and 0.2 wt % magnesium stearate. The semipermeable wall comprises 95 wt % cellulose acetate comprising a 39.8% acetyl content, and 5.0 wt % polyethylene glycol comprising a 3350 molecular weight. The dosage form comprises two passageways, 25 mils (0.635 mm), and it had a tandospirone citrate mean release rate of 14.53 mg/hr. Accompanying FIG. 7A depicts the cumulative amount of tandospirone citrate released by the dosage form.

EXAMPLE 13

A dosage form comprising 176 mg of tandospirone citrate is made as follows: first, 12.50 kg of micronized tandospirone citrate, 8.438 kg of poly(ethylene oxide) having a 200,000 molecular weight, and 2.813 kg of poly(ethylene oxide) having a 300,000 molecular weight, are added to a Freund Flo-Center's® bowl, a fluid bed granulator. The bowl was attached and granulation process was initiated for effecting granulation. Next, the dry powders were air suspended and mixed for 6 minutes. Then, a solution prepared by dissolving 500 g of poly(vinylpyrrolidone) identified as K29-32 having an average molecular weight of 40,000, in 8,000 g of water was sprayed from 3 nozzles onto the powder. The coating conditions were monitored during the process of aqueous poly(vinylpyrrolidone) as follows: solution spray rate of 125 g/min from each nozzle for a total spray rate of 375 g/min; inlet temperature 45° C.; and process air flow of 1000 cfm.

The coating process was computerized and automated in cycles. Each cycle contained 30 seconds of solution spraying followed by two seconds of drying and 10 seconds of filter bags shaking to unglue and possible powder deposits. At the end of the solution spraying the coated granulated particles were continued with the drying process for 25 minutes. The machine was turned off, and the coated granules were removed from the Flo-Coater. The coated granules were sized using a Fluid Air Mill. The granulation was transferred to a Rotocone®, mixed and lubricated with 250 g of magnesium stearate and mixed with 12.5 g of butylated hydroxytoluene.

Next, a push composition is prepared as follows: first, 415.5 g of pharmaceutically acceptable poly(ethylene oxide) comprising a 7,500,000 molecular weight, 150 g of sodium chloride and 6 g of ferric oxide separately are screened through a 40 mesh screen. Then, all the screened ingredients are mixed with 30 g of hydroxypropylmethylcellulose comprising a 11,200 molecular weight to produce a homogeneous blend. Next, 300 mg of denatured anhydrous alcohol is added slowly to the blend with continuous mixing for 5 minutes. The freshly prepared wet granulation is passed through a 20 meshy screen, allowed to dry at room temperate for 16 hours, and again passed through a 20 mesh screen. The screened granulation is mixed with 1.5 g of magnesium stearate in a rollermill for 5 minutes.

Next, the tandospirone citrate drug composition and the push composition are compressed into bilayered tablets. First, 352 mg of the tandospirone composition is added to a punch and tamped, then, 175 mg of the push composition is added and the layers are pressed under a pressure head of two tons into a 7/16" (1.11 cm) diameter contacting layered arrangement.

The bilayered arrangements are coated with a semipermeable wall. The wall forming composition comprises 95% cellulose acetate having a 39.8% acetyl content, and 5% polyethylene glycol having a molecular weight of 3350. The wall-forming composition is dissolved in an acetone:water (95.5 wt:wt) cosolvent to make a 4% solids solution. The wall forming composition is sprayed onto and around the bilayers in a 24" (60 cm) Vector Hi-Coater.

Figure 7B:
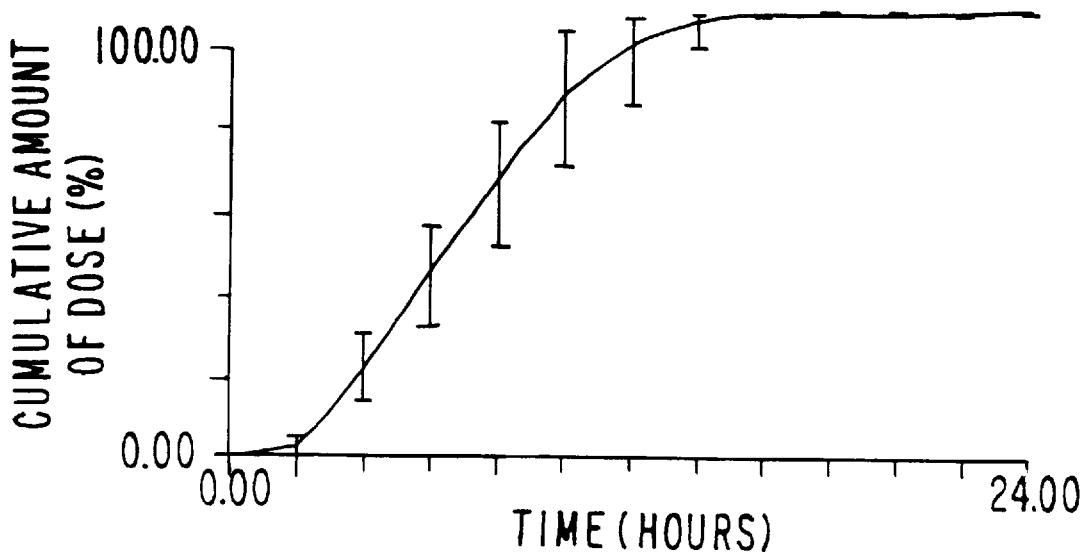

Next, two 25 mil (0.635 mm) exit passageways are mechanically drilled through the semipermeable wall to connect the drug layer with the exterior of the dosage form. The residual solvent is removed by drying for 48 hours at 50° C. and 50% humidity. Next, the osmotic dosage form is dried for 1 hour at 50° C. to remove excess moisture. The dosage form produced by this manufacture provides 50 wt % tandospirone citrate, 33.75 wt % of poly(ethylene oxide) having a 200,000 molecular weight, 11.25 wt % of poly (ethylene oxide) comprising a 300,000 molecular weight, 4 wt % poly(vinyl pyrrolidone) possessing a 40,000 molecular weight, 0.95 wt % magnesium stearate, and 0.05 wt % butyl hydroxytoluene. The push composition comprises 68.8 wt % poly(ethylene oxide) comprising a 7,500,000 molecular weight, 25 wt % sodium chloride, 5 wt % hydroxypropylmethylcellulose possessing 11,200 molecular weight, 1.0 wt % ferric oxide and 0.2 wt % magnesium stearate. The semipermeable wall comprises 95 wt % cellulose acetate comprising a 39.8% acetyl content, and 5.0 wt % polyethylene glycol comprising a 3350 molecular weight. The dosage form comprises two passageways, 25 mils (0.635 mm), and it had a tandospirone citrate mean release rate of 17.24 mg/hr. Accompanying FIG. 7B depicts the cumulative dose released over 24 hours. The above examples provide continuous release dosage forms that provide for the extended release of 1 mg/hr to 20 mg/hr over 24 hours of tandospirone pharmaceutically acceptable salt for treating depressive disorders in a patient in need of tandospirone therapy. New Example 13 illustrates the advantage of a polymer blend in drug layer 16 at a drug loading above 45 wt %. Examples 12 and 13 by comparison illustrate that a poly(ethylene oxide) possesses a lower molecular weight, for example 200,000, exhibits a quicker start-up time and delivers a greater concentrate of drug in a comparable period of time.

EXAMPLE 14

A bioerodible dosage form is provided as follows: To 375 mg of poly(2.2-dioxo-trans-1,4-cyclohexane dimethylane tetrahydrofuran) is added 125 mg of tandospirone citrate with heating in a Teflon® coated pan to about 150° C., with good mixing to yield a homogenous blend. After the pan cooled to room temperature, the polymer tandospirone drug formulation is removed from the pan and a solid dosage form of oval shape is prepared by pressing at 121° C. and at 10,000 psi for 5 minutes to yield the dosage form.

EXAMPLE 15

A diffusion dosage form is prepared by blending 175 mg of tandospirone with 270 mg of poly(dimethylsiloxane) and molded into an oval shaped core. Next, molecularly bi-axially oriented heat shrinkable polytethylene) film of 2 mil thickness is embossed around the core and the diffusion film heated for 3 minutes at 300° F. resulting in a diffusional release rate film surrounding a reservoir core containing tandospirone that is released at a diffusion controlled rate over 24 hours.

EXAMPLE 16

A diffusion controlled dosage matrix is prepared by following the above procedures, with copolymer ethylene-vinyl acetate having an acetate content of 40% dissolved in methylene chloride, to which is added tandospirone, and film cast onto a glass substrate mold. The solvent is allowed to evaporate at room temperature and the molded form warm air dried to yield the dosage form.

DISCLOSURE OF USE OF THE DOSAGE FORM FOR PERFORMING A METHOD OF PRACTICING THE INVENTION

A embodiment of the invention pertains to the use of the dosage form provided by the invention in a method for delivering a drug of formula 1 at a controlled rate orally to a warm-blooded animal in need of drug formula 1 therapy, wherein the use comprises the steps of: (A) admitting into the warm-blooded animal a dosage form comprising: (1) a wall surrounding a compartment, the wall comprising a semipermeable polymeric composition permeable to the passage of fluid and substantially impermeable to the passage of drug; (2) a drug layer in the compartment comprising a formulation comprising a dosage unit amount of the drug of the formula:

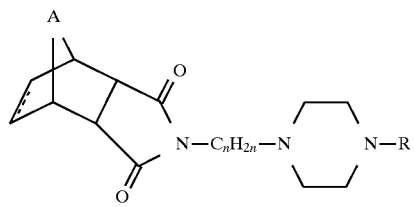

for performing a therapeutic program; (3) a push layer in the compartment comprising an osmotic formulation for imbibing and absorbing fluid for expanding in size for pushing the drug of the formula from the dosage form; (4) at least one osmotic dimensioned passageway in the wall for releasing the drug; (B) imbibing fluid through the semipermeable wall at a fluid rate determined by the permeability of the semipermeable wall and the osmotic pressure across the semipermeable wall causing the push layer to expand; and (C) delivering the therapeutically active drug from the dosage form through the exit passageway to the warm-blooded animal over a prolonged period of time up to 24 hours. The drug to the formula is administer by the method of the invention for treating depressive disorders, including major depression—single or recurrent, bipolar disorder—depressed depressive disorders, dysthymia, major depression with our without melancholia, or cyclothymia as characterized by alternate lively and depressed moods. The drug can be in the exo form as follows:

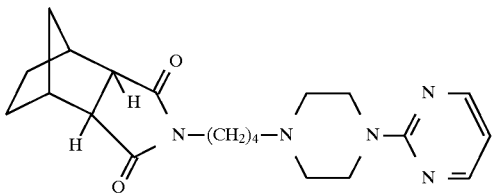

or, the drug can be in the endo form as follows:

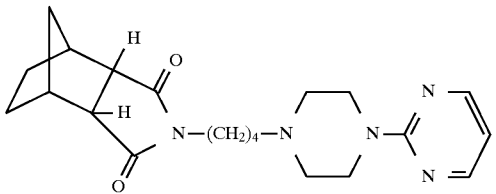

or the drug can be a mixture of the exo and the endo forms.

Another embodiment of the invention is to provide a method for delivering tandospirone comprising admitting orally into a patient a dosage form comprising 1 mg to 750 mg of tandospirone that is administered over 24 hours by at least one of rate-controlled diffusion, rate-controlled bioerosion, or rate-controlled ion-exchange to the patient for treating a depressant state in the patient needing tandospirone therapy.

Dosage form 10 of this invention, as seen from the above disclosure and in the above drawing figures, can be used in a method for administering a drug by the oral route, and in another method, the dosage form can be sized and shaped for administering a drug by the sublingual and buccal routes. The sublingual and buccal routes can be used for quicker therapy and they can be used when a smaller dose of drug is needed for therapy. The latter routes can be used as a by-pass of the first pass of hepatic metabolism of the drug. The drug of figure (1) and (2) can be administered by the sublingual or buccal routes can be used for administering the drug for the management of anxiolytic patients.

In summary, it will be appreciated that the present invention contributes to the art an unobvious dosage form that possesses practical utility, can administer a drug at a dose metered release rate per unit time. While the invention has been described and pointed out in detail with reference to operative embodiments thereof, it will be understood by those skilled in the art that various changes, modifications, substitutions and omissions can be made without departing from the spirit of the invention. It is intended, therefore, that the invention embraces those equivalents within the scope of the claims which follow.

We claim:

1. A method for treating depression in a patient in need of therapy, wherein the method comprises: admitting orally into the patient a solid dosage form selected from the group consisting of osmotic, diffusion, bioerosion and ion-exchange comprising 1 mg to 750 mg of a member selected from the group consisting of tandospirone and its pharmaceutically acceptable salts, which member is administered at a dosage controlled-rate of 1 mg to 20 mg per hour over a period of 24 hours by the dosage form to provide antidepressant therapy in the patient.

2. The method for treating depression in a patient according to claim 1, wherein the pharmaceutically acceptable salt is a citrate.

3. A method for treating depressant disorders in a patient in need of antidepressant therapy, wherein the method comprises the step of: orally admitting into the patient a solid dosage form selected from the group consisting of osmotic, diffusion, bioerosion and ion-exchange comprising 1 mg to 750 mg of tandospirone; administering the tandospirone to the patient; and wherein the method is characterized in that the rate of release of 1 mg to 20 mg per hour of tandospirone versus time up to 24 hours is dosage form controlled tandospirone administration to the patient.

4. A method for treating anxiety in a patient in need of anti-anxiety therapy, where the method comprises: admitting orally a solid dosage form comprising 1 mg to 750 mg of anti-anxiety tandospirone into the patient that is administered at a dosage form controlled rate of 1 mg to 20 mg per hour by a method selected from the group consisting of osmotic, diffusion, bioerosion and ion-exchange over an extended period to provide anti-anxiety tandospirone therapy to the patient.

5. The method for treating anxiety in a patient in need of anti-anxiety therapy, wherein the tandospirone is tandospirone citrate.

* * * * *